United States Patent [19]
Marian, Jr.

[11] Patent Number: 5,617,866
[45] Date of Patent: Apr. 8, 1997

[54] MODULAR TRANSDUCER SYSTEM

[75] Inventor: Vaughn R. Marian, Jr., Saratoga, Calif.

[73] Assignee: Acuson Corporation, Mountain View, Calif.

[21] Appl. No.: 584,332

[22] Filed: Jan. 5, 1996

[51] Int. Cl.$^6$ .............................. A61B 8/00; H05K 1/00
[52] U.S. Cl. ................................ 128/662.3; 439/66
[58] Field of Search .................... 128/662.03; 439/55, 439/63–66

[56] References Cited

U.S. PATENT DOCUMENTS

| | | | |
|---|---|---|---|
| 4,550,607 | 11/1985 | Maslak et al. | 73/626 |
| 4,699,009 | 10/1987 | Maslak et al. | 73/626 |
| 4,774,568 | 9/1988 | Matsuo | 358/98 |
| 5,116,237 | 5/1992 | Loewen | 439/326 |
| 5,190,473 | 3/1993 | Mroczkowski et al. | 439/580 |
| 5,308,252 | 5/1994 | Mroczkowski | 439/66 |
| 5,310,352 | 5/1994 | Mroczkowski et al. | 439/76 |
| 5,358,411 | 10/1994 | Mroczkowski | 439/66 |
| 5,402,791 | 4/1995 | Saitoh et al. | 128/662.03 |
| 5,410,208 | 4/1995 | Walters et al. | 310/334 |
| 5,415,175 | 5/1995 | Hanafy et al. | 128/662.03 |
| 5,417,578 | 5/1995 | Mroczkowski et al. | 439/101 |

OTHER PUBLICATIONS

R. Rothenberger and R.S. Mroczkowski, *High Density Zero Insertion Force Microcoaxial Cable Interconnection Technology*, AMP Inc.

*Primary Examiner*—Francis Jaworski
*Attorney, Agent, or Firm*—Hopkins & Carley

[57] ABSTRACT

A modular transducer system includes a small, hand held adapter which remains permanently attached to an ultrasound system console and permits the rapid connection and disconnection of individual, sterilizable ultrasound transducers. In a preferred embodiment, the hand held adapter is connected to the system by a retractable cable. In another preferred embodiment, the individual transducers are identifiable by the system using transducer generated binary codes. The individual transducers are submersible in a wide variety of liquids including cleaning solutions and disinfectants. The small transducers are easily stored at the site of the ultrasound examination. Bulky, awkward, time consuming cables and connectors are eliminated.

40 Claims, 13 Drawing Sheets

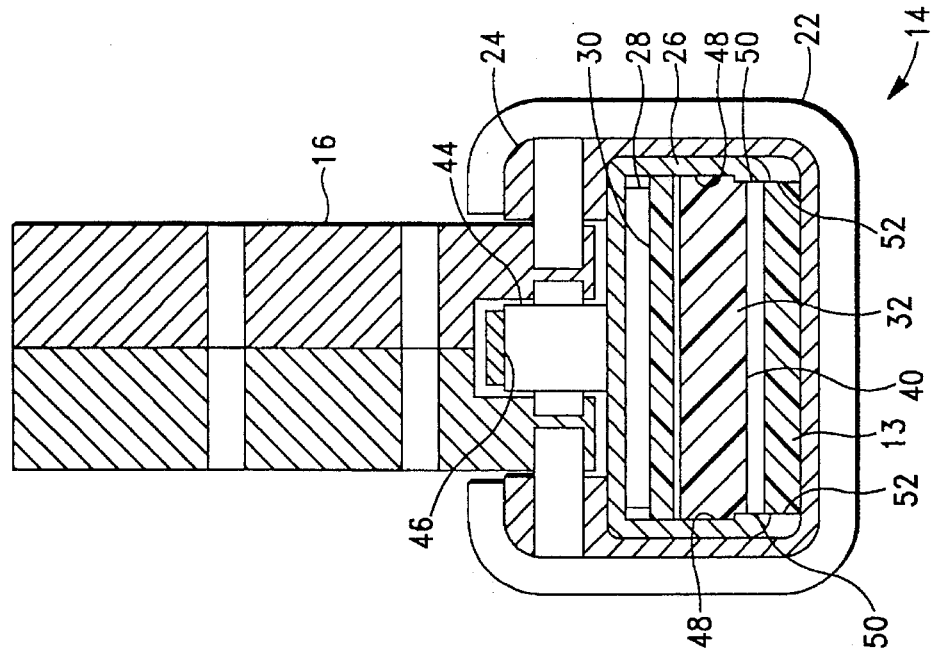
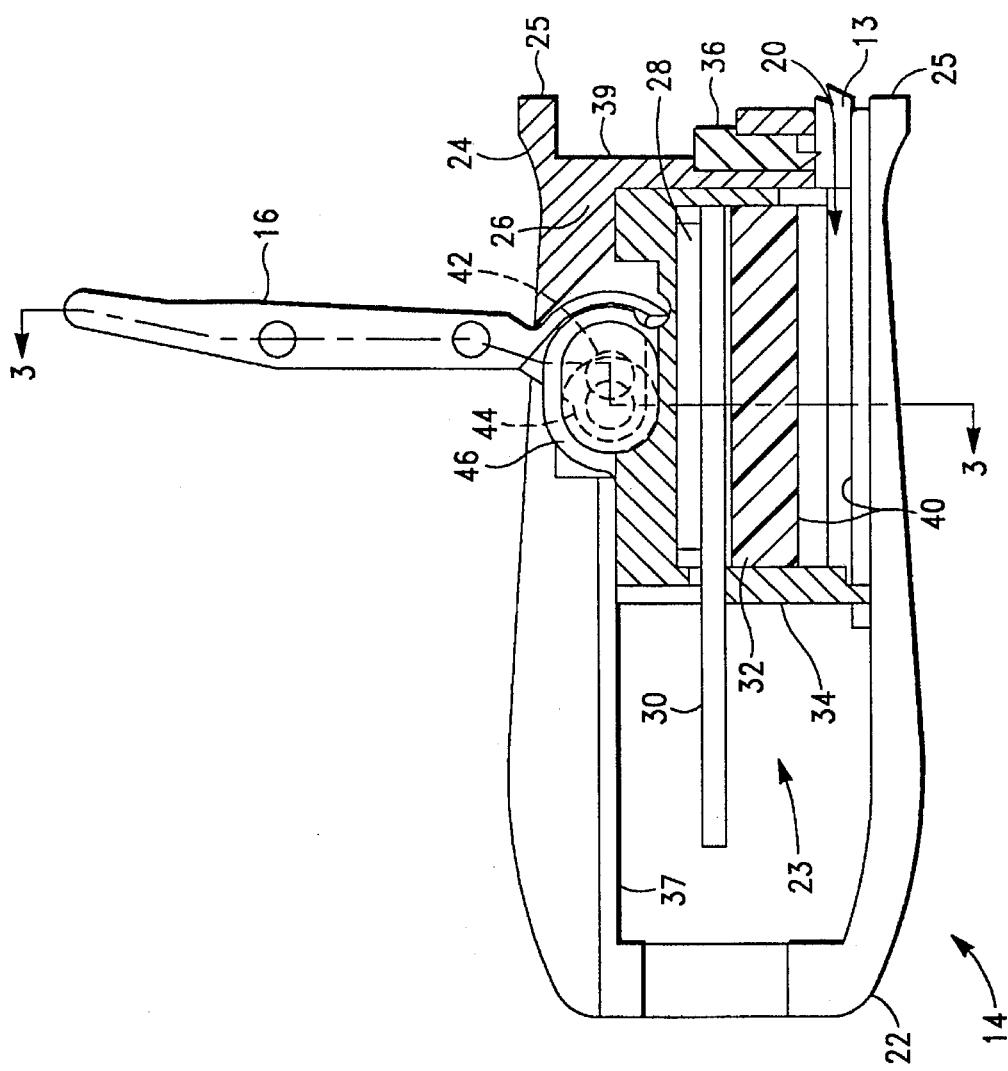

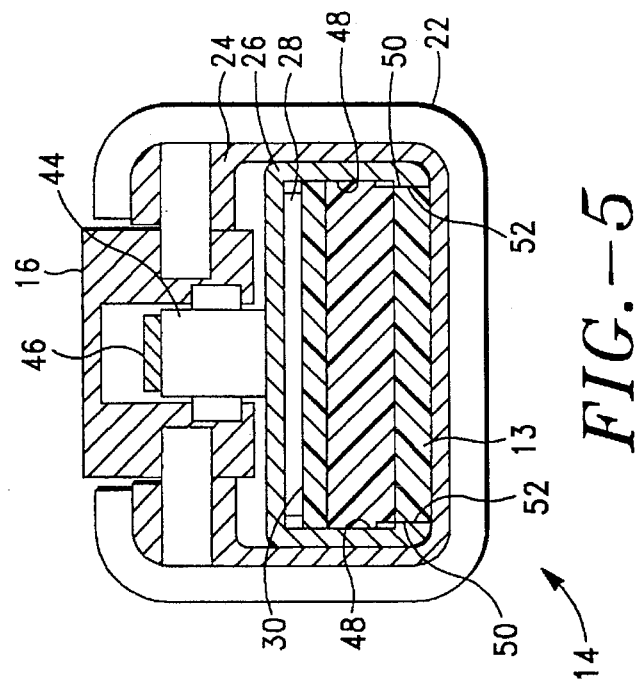
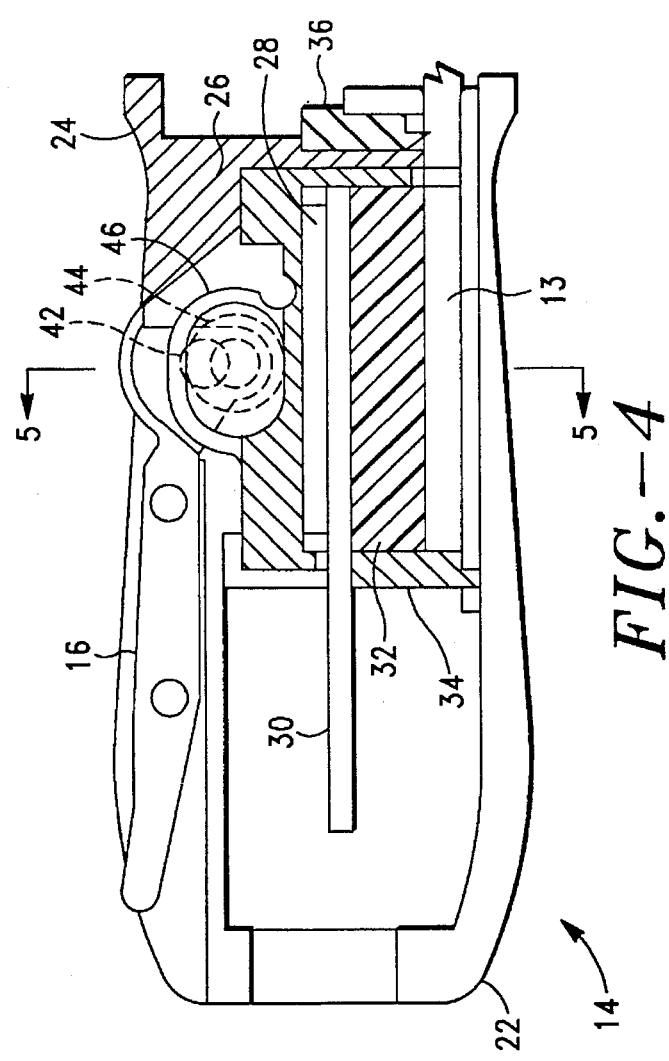

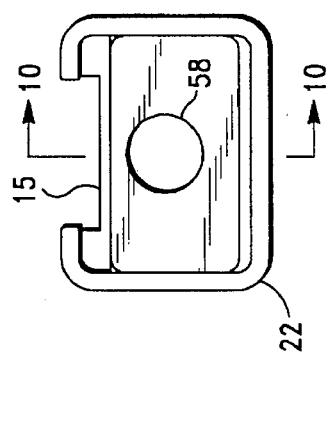
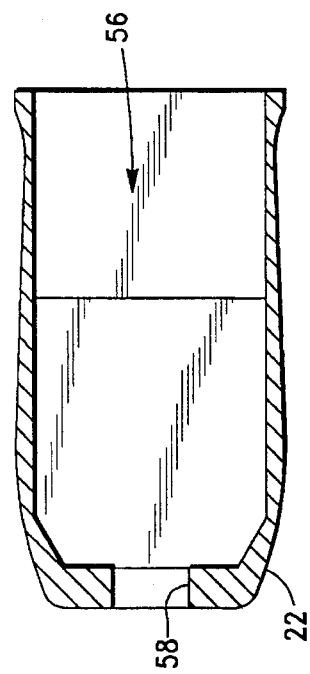
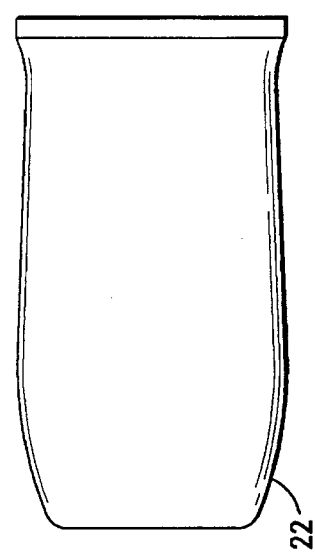
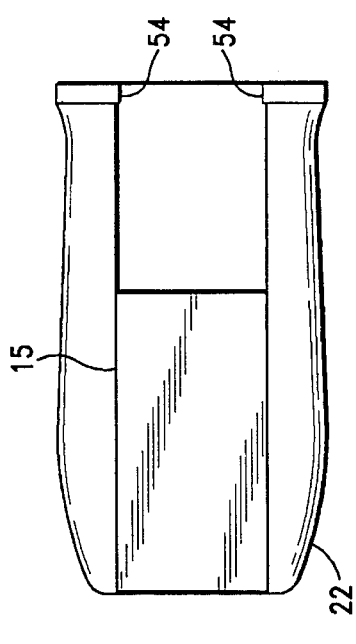
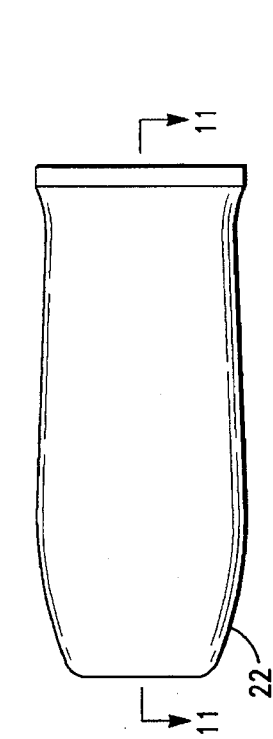

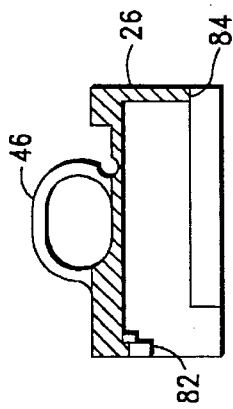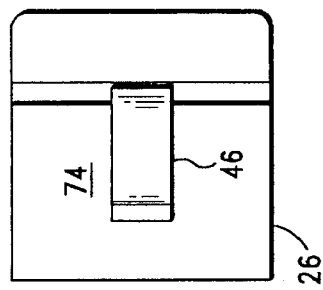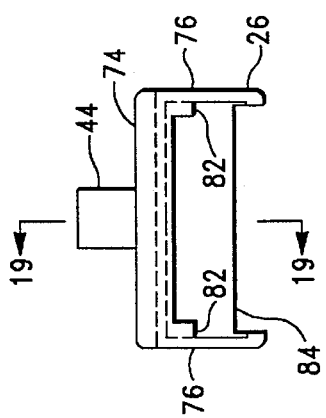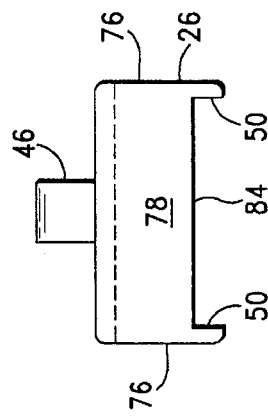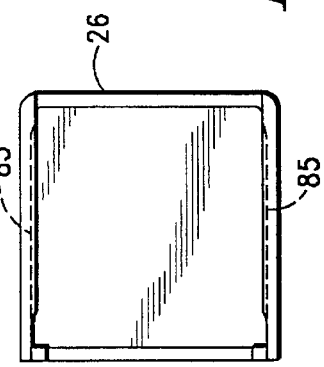

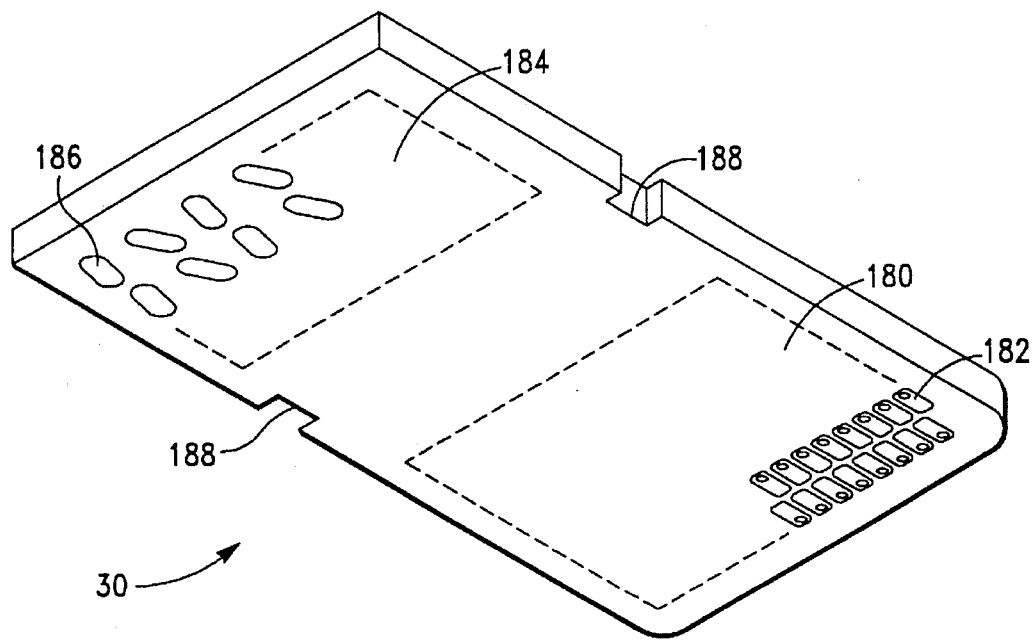
FIG.−30
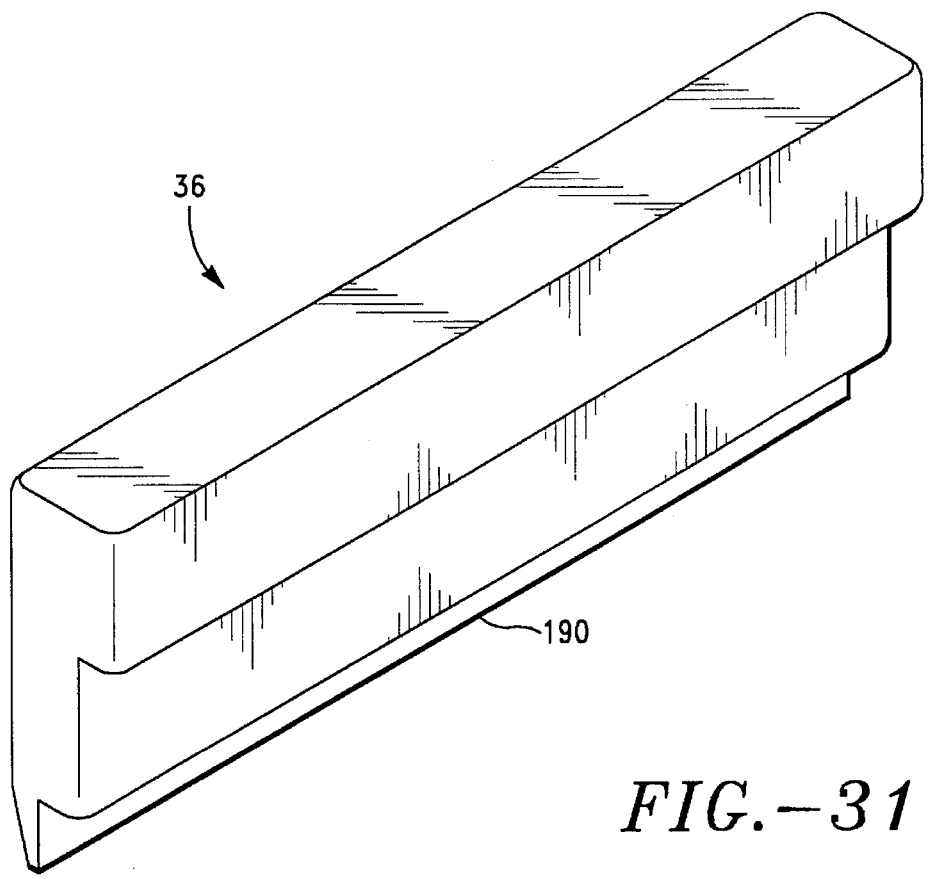
FIG.−31

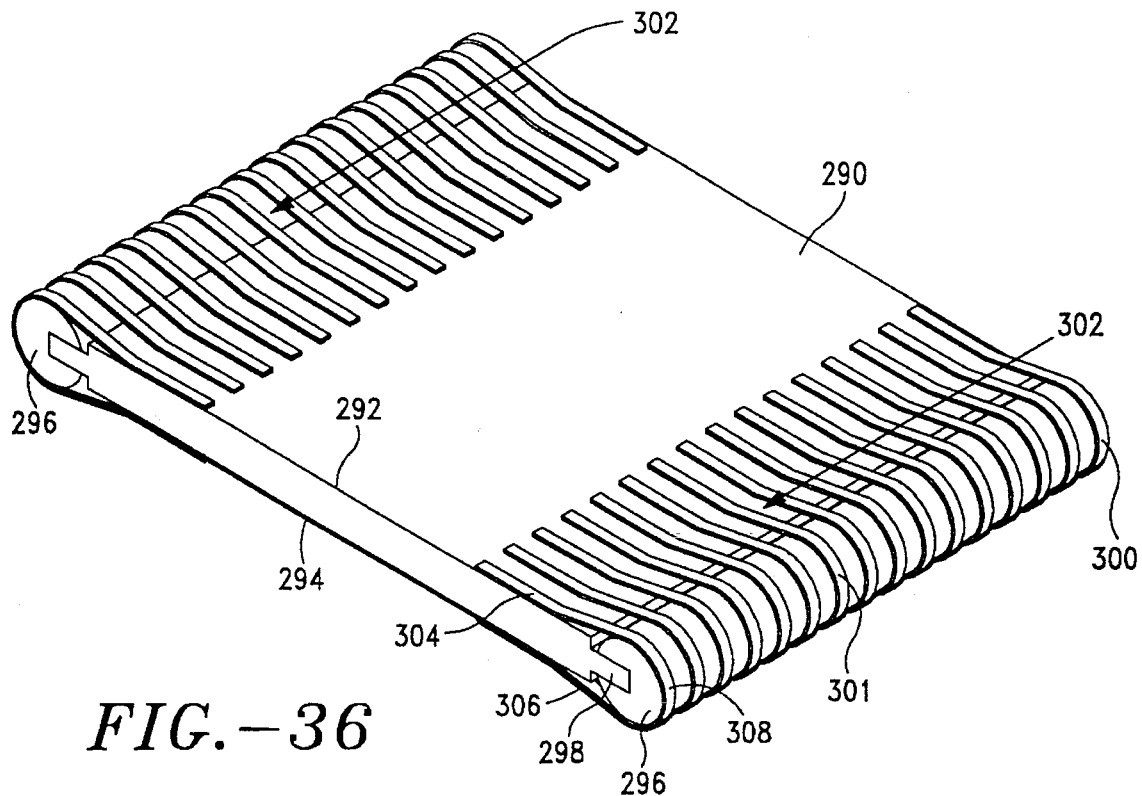
FIG.—36
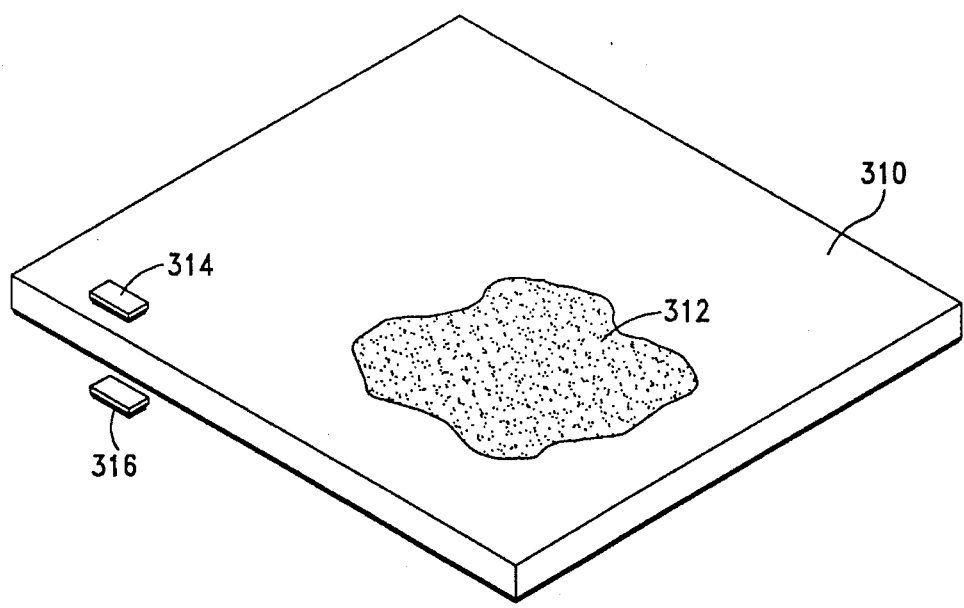
FIG.—37

MODULAR TRANSDUCER SYSTEM

BACKGROUND OF THE INVENTION

1. Field of the Invention

This invention relates generally to the field of ultrasound imaging systems and more particularly to a modular ultrasound transducer system employing easily interchangeable transducer elements.

2. Previous Art

Ultrasound imaging systems are popular in the health care field because they allow a health care provider to electronically display images of the interior of the human body in a safe, non-invasive manner.

To obtain these images, the health care provider selects an ultrasound transducer—a device often small enough to be held in the hand, like an electric razor—and connects the transducer to a special computer. When placed against the patient's skin, or safely inside one of the body's openings, the transducer emits a burst of ultra-high frequency sound waves into the body. A fraction of a second later, the sound waves are reflected back into the transducer by internal body organs, producing weak electrical signals. These weak signals are returned to the computer through a cable, are amplified, and are converted into a displayed image of the internal organs.

There are a variety of transducers, each useful for viewing a particular part, or parts, of the body. Typically, each transducer is connected to a long cable which has a connector at one end for attachment to the system console.

An examination using ultrasound may involve the use of many transducers, each having its own cable and connector. The health care provider must select a particular transducer, then attach its connector to the computer. Then select another transducer, disconnect the first transducer from the computer and connect the new transducer, and so on.

Many of the electrical connectors used to attach ultrasound transducer cables to the system are bulky, complex, difficult to store and awkward to manipulate. Thus, changing from one transducer to the next can markedly slow the pace of an ultrasound examination. Also, it is necessary to store the transducers and their cables and connectors near the place where the examination is being conducted. These stored cables and connectors present a possibility for contamination since they are not easily sterilizable.

Because of the problems of physical access, storage, and cleanliness associated with the use of typical ultrasound transducers, it is desirable to have an ultrasound transducer in which the storage and cleanliness problems are overcome. Moreover, it is very desirable to have a family of hand held transducers which are easily and rapidly connected and disconnected from the ultrasound system.

SUMMARY OF THE INVENTION

It is an object of the present invention to provide a family of hand held ultrasound transducers which share a single, common cable and system connector.

It is a further object of this invention to provide such a common cable having a quick disconnect receptacle built into a hand held portion and enabling rapid interchange of a variety of compatible ultrasound transducers.

It is a further object of this invention to provide a modular transducer system which solves both the storage and the connect/disconnect problems by having interchangeable transducers share a common cable which remains connected to the ultrasound system console computer.

In accordance with the above objects and those that will be mentioned and will become apparent below, the modular transducer system in accordance with this invention comprises:

an ultrasound transducer module including an ultrasound transducer and a transducer printed wiring board, the transducer board having a plurality of electrical contact pads disposed on a portion of one surface and connected for carrying electrical signals between the pads and the transducer;

a system printed wiring board, the system board having a plurality of electrical contact pads disposed on a portion of one surface in corresponding opposition to contact pads of the transducer board and defining opposed pairs of contact pads, the system board having wiring termination pads spaced apart from the contact pads, and predetermined contact pads being electrically connected with predetermined wiring termination pads;

an assembly of electrical contact springs defining a contact module located between the transducer board and the system board, the contact springs being aligned between opposed pairs of contact pads;

aligning and clamping means for supporting the system board, the contact module, and the transducer board, for aligning the opposed pairs of contact pads with corresponding contact springs, and for clamping the contact pad portion of the transducer board and the system board to the contact module, causing the opposed contact pads to compress the aligned contact springs, whereby an electrical connection is established between the system connector and the ultrasound transducer, and the transducer module is supported by the aligning and clamping means.

In a preferred embodiment, the modular transducer system includes a plurality of interchangeable ultrasound transducer modules, the individual modules having predetermined acoustic characteristics and identifiable to the system console by self contained binary codes.

The preferred embodiment includes a convenient; hand held receptacle assembly for attaching individual modules to the system console cable. The receptacle assembly has an operating handle for locking and unlocking the individual modules and for establishing electrical connection between the module and the system console.

Another preferred embodiment includes a compact ultrasound transducer module which is sealed to prevent fluids from damaging the transducer and electrical connections. The modules are submersible in a wide variety of liquids including cleaning solutions and disinfectants.

It is an advantage of this invention to permit the rapid interchange of a variety of sterilized transducer modules, easily stored at the examination site, without the need to handle awkward and time consuming cable and connector changes. And the sterilized transducer modules do not have to be sheathed in latex or plastic.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein:

FIG. 2 is a side, cross-sectional view illustrating an unlocked position of a receptacle assembly of the modular transducer system of FIG. 1.

FIG. 3 is an end, cross-sectional view taken through FIG. 2 along the line 3—3, looking in the direction of the arrows.

FIG. 4 is a side, cross-sectional view of the receptacle assembly shown in a locked position.

FIG. 5 is an end, cross-sectional view taken through FIG. 4 along the line 5—5, looking in the direction of the arrows.

FIGS. 6–11 illustrate a housing for the receptacle assembly of FIG. 2. FIG. 6 is a top view of the housing.

FIG. 7 is a side view of the housing.

FIG. 8 is a view taken from the right hand end of FIG. 7.

FIG. 9 is a bottom view of the housing.

FIG. 10 is a side, cross-sectional view of the housing taken along the line 10—10 of FIG. 8, looking in the direction of the arrows.

FIG. 11 is a top, cross-sectional view taken along the line 11—11 of FIG. 7, looking in the direction of the arrows.

FIG. 12 is a top view of the frame.

FIG. 13 is a side, cross-sectional view of the frame, taken along the line 13—13 of FIG. 14, looking in the direction of the arrows.

FIG. 14 is an end view of the frame taken from the left end of FIG. 15.

FIG. 15 is a side view of the frame.

FIG. 16 is an end view of the frame taken from the right end of FIG. 15.

FIG. 17 is a bottom view of the frame.

FIGS. 18–23 illustrate a slide, part of the receptacle assembly of FIG. 2.

FIG. 18 is a top view of the slide.

FIG. 19 is a side, cross-sectional view of the slide taken along the line 19—19 of FIG. 20 and looking in the direction of the arrows.

FIG. 20 is an end view of the slide, from the left end of FIG. 21.

FIG. 21 is a side view of the slide.

FIG. 22 is an end view of the slide, from the right end of FIG. 21.

FIG. 23 is a bottom view of the slide.

FIG. 24 is a side view of the retainer from the left side of FIG. 25.

FIG. 25 is a plan view of the retainer.

FIG. 28 is a profile, cross-sectional view of one embodiment of the ultrasound transducer module.

FIG. 29 is a side, cross-sectional view of the ultrasound transducer module shown in FIG. 28.

FIG. 30 is a perspective view from the bottom, contact, side of a system printed wiring board, part of the receptacle assembly of FIG. 2, and illustrating several contact pads and several wiring termination pads.

FIG. 31 is a perspective view of a molded rubber wiper, part of the receptacle assembly of FIG. 2.

FIG. 36 is a partial perspective view of a contact module using flex circuit to connect opposed contact pads.

FIG. 37 is a partial perspective view of a contact module using a Z-axis material.

DETAILED DESCRIPTION OF THE PREFERRED EMBODIMENT

Figure 1:
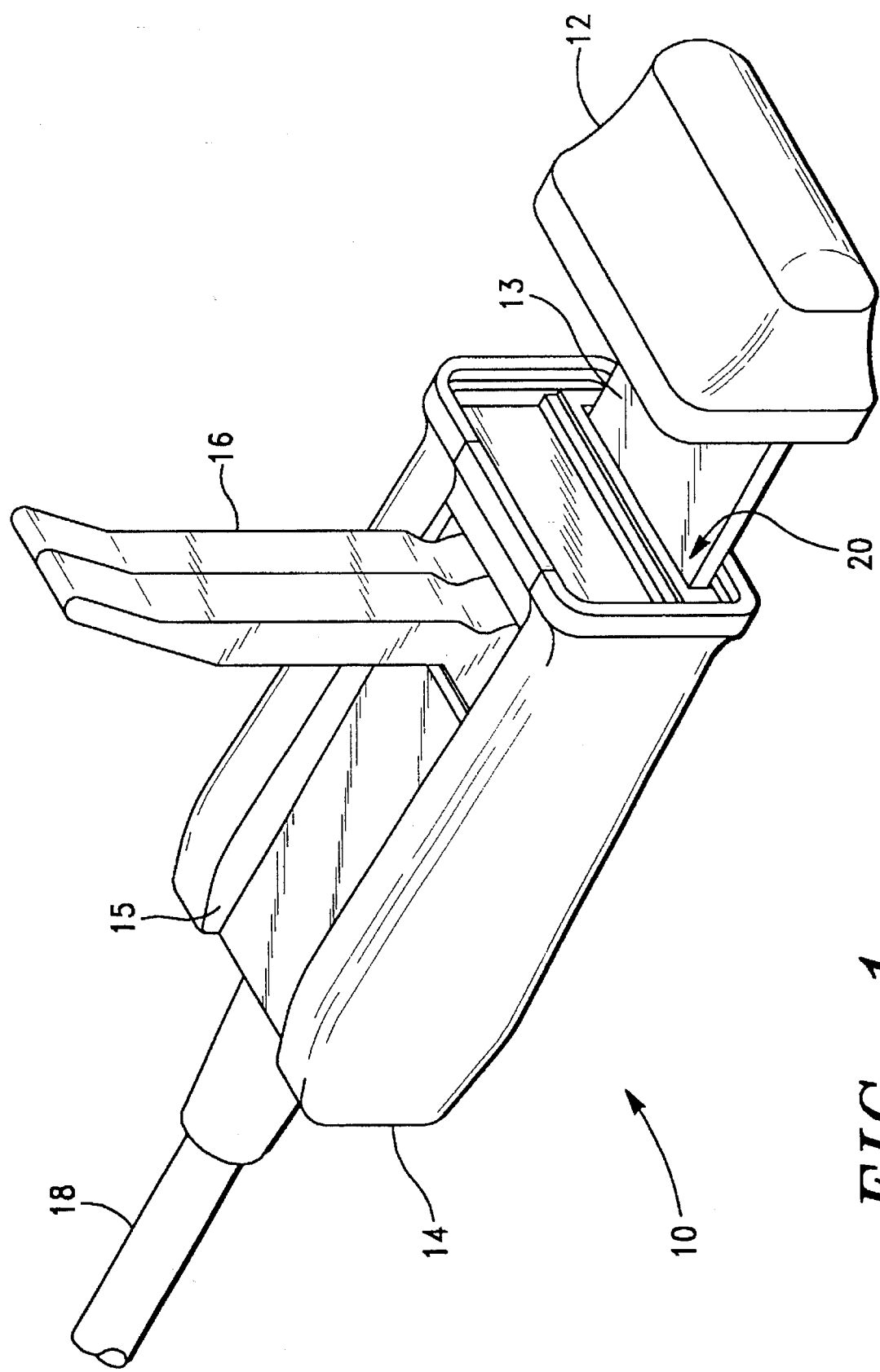
FIG. 1 is a perspective view illustrating a modular transducer system according to one aspect of the present invention.

The invention will now be described with respect to FIG. 1, a perspective view of a modular transducer system according to one aspect of the present invention, and depicted generally by the numeral 10. The major components of the modular transducer system 10 include an interchangeable ultrasound transducer module 12, a receptacle assembly 14, and a microcoaxial cable assembly 18 for connection to an ultrasound system console (not shown).

The receptacle assembly 14 includes a locking/unlocking handle 16, illustrated here in the "unlocked" position. The handle 16 is rotatable into a recess 15 in the body of the receptacle assembly 14, defining a "locked" position.

The interchangeable ultrasound transducer module 12 includes a printed wiring board 13. The board 13 is insertable into an opening 20 in one end of the receptacle assembly 14 when the handle 16 is in the unlocked position. Rotation of the handle 16 to the locked position clamps the printed wiring board 13 within the receptacle assembly 14, establishing electrical connections between the microcoaxial cable assembly 18 and the ultrasound transducer module 12.

One preferred embodiment of the modular transducer system 10 includes interchangeable ultrasound transducer modules. Each ultrasound module has a predetermined acoustic characteristic. During the course of a medical examination, a practitioner will exchange ultrasound modules to obtain the most advantageous acoustic characteristic for making a correct diagnosis.

One transducer module 12 is exchanged for another by rotating the handle 16 from the locked to the unlocked position, withdrawing the printed wiring board 13 from the receptacle assembly 14, inserting the printed wiring board of the other ultrasound module and, finally, rotating the handle 16 back to the locked position.

The modular transducer system 10 permits a single cable assembly 18 to remain attached to the ultrasound imaging console while the practitioner selects appropriate transducer modules to complete a medical examination. In one preferred embodiment of the system, the cable assembly 18 is permanently attached to an ultrasound console. In another preferred embodiment, the cable assembly 18 is attached to the console via a retractable reel.

Additionally, the small size of the individual ultrasound transducers 12 permits them to be stored conveniently at the examination area. Each ultrasound transducer module is sealed and is submersible in a wide variety of liquids including cleaning solutions and disinfectants. The cleaning solutions include soap and water or isopropyl alcohol. The liquid disinfectants include CIDEX™ (trademark of Johnson and Johnson Medical, Inc.), which is a 2% solution of glutaraldehyde salt in water, or STERIS 20™ (trademark of STERIS Corp.), which is a proprietary aqueous solution, peroxyacetic acid being the active ingredient. Both of these disinfectants are described in greater detail in the Appendix cited below.

The disclosures of each of the following references are believed to be useful to an understanding of the present invention. The following printed materials are therefore incorporated by reference herein: a U.S. patent application entitled "Submersible Connector System," including an Appendix, filed Oct. 4, 1995, as Ser. No. 08/538,870, assigned to the assignee of the present invention; U.S. Pat. Nos. 4,550,607, 4,669,009, 5,190,473, 5,308,252, 5,310,352, 5,358,411 and 5,417,578; and an AMP Incorporated publication by R. Rothenberger et al., entitled "High-Density Zero Insertion Force Microcoaxial Cable Interconnection Technology."

RECEPTACLE ASSEMBLY, FIGS. 2–5

The invention will now be described with respect to FIGS. 2–5 which illustrate aspects of the receptacle assembly 14. In particular, these figures illustrate how the parts of the receptacle assembly cooperate to define a receiving space for the transducer printed wiring board 13, how the board 13 is clamped and released from that space, and how an electrical connection is established between the microcoaxial cable assembly 18 and the ultrasound transducer.

FIG. 2 is a side, cross-sectional view illustrating the receptacle assembly 14 of the modular transducer system 10 of FIG. 1. The receptacle assembly 14 includes a plastic housing 22, and a subassembly 23 including the locking/unlocking handle 16, a frame 24, a slide 26, a rubber load pad 28, a system printed wiring board 30, a contact module 32, a retainer 34, and a wiper 36. The plastic housing 22 has a hollow interior 37 into which the subassembly 23 is placed during manufacture.

The frame 24 forms an enclosure within which the slide 26 is free to move a short distance in the vertical direction (relative to the orientation of the parts in FIG. 2). When the handle 16 is in the unlocked (upward) position as illustrated in FIG. 2, the slide 26 is at the upper limit of its travel. The rubber load pad 28, the system printed wiring board 30 and the contact module 32 are each located inside the hollow slide 26 and follow the movement of the slide 26 within the frame 24. The frame is closed at one end 39 and a retainer 34 is fitted into the frame 24 to close off the opposite end, to retain the slide 26 within the frame 24, and to retain the rubber load pad 28, the system printed wiring board 30 and the contact module 32 within the slide 26.

Both the frame 24 and the slide 26 include an opening 20 at the end opposite the retainer 34 to permit the insertion of the transducer module printed wiring board 13. In FIG. 2 a portion of the transducer printed wiring board 13 is shown inserted into the opening 20. A board receiving space 40 is defined within the frame 24 and the slide 26, and is located between a bottom surface of the contact module 32 and an upper surface of a bottom portion of the frame 24. The opening 20 provides access to the receiving space 40.

In one embodiment of the invention, the retainer 34 establishes a limit to the inward travel of the inserted board 13, while in another embodiment, the insertion distance is determined by portions 25 of the frame 24 and the plastic housing 22.

The system printed wiring board 30 has electrical contact pads (not shown) on the surface adjacent to the contact module 32. The transducer printed wiring board 13 has corresponding opposed contact pads on the surface adjacent to the contact module 32. As the handle 16 is rotated from the unlocked position toward the locked position (illustrated in FIGS. 4 and 5) the slide 26 moves downward within the frame 24.

As the slide 26 moves downward, it compresses the rubber load pad 28, distributing the force across the upper surface of the system printed wiring board 30. The system board 30 is forced downward against the contact module 32 so that the compliant contact springs (not shown) begin to deform under load. At the same time, the contact module 32 is lowered within the receiving space 40 so that its bottom surface and the lower portion of the contact springs come into contact with the corresponding opposed transducer printed wiring board contact pads (not shown). As the rotation of the handle 16 continues toward the locked position, the deformed contact springs make a wiping action across the corresponding contact pads, establishing a reliable electrical connection between the cable assembly 18 and the ultrasound transducer (see U.S. Pat. Nos. 5,308,252 and 5,358,411).

In the locked position, the handle 16 is fully rotated into the recess 15 and the slide 26 is at the bottom of its limited travel within the frame 24. The rubber load pad 28 is fully compressed and the system printed wiring board 30, whose thickness is limited to provide a compliant member, the contact module 32, and the transducer printed wiring board 13 are clamped together.

The handle 16 is pivoted about a dowel pin 42 in the frame 24, and is shown in FIG. 2 in the unlocked position, extending upwardly from the receptacle assembly 14. The handle 16 includes a needle bearing 44 having a center offset from the dowel pin 42. As mentioned above, the slide 26 moves up and down within the frame 24. A cam 46 located at the top of the slide 26 engages the offset needle bearing 44. When the handle 16 is rotated, the offset needle bearing 44 moves in an arc about the dowel pin 42, causing the cam to follow. The slide 26 is constrained by the frame 24 to move within the frame in a vertical direction. As the handle is rotated in a counter clockwise direction from the unlocked position shown in FIG. 2, the needle bearing 44 moves through its arc, carrying the cam 46 downward and bringing the contact springs (not shown) within the contact module 32 into electrical contact with the opposed contact pads (not shown) on the two printed wiring boards 30, 13.

Figure 12:
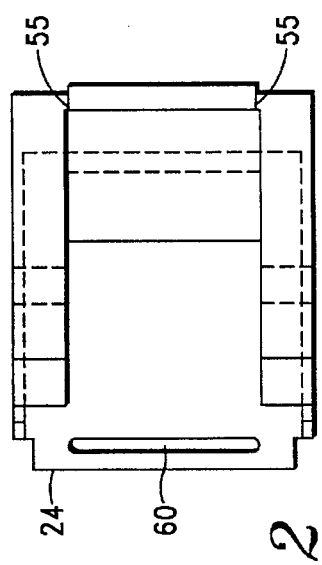

During assembly, the load pad 28, the system printed wiring board 30 and the contact module 32 are assembled within the slide 26, as shown, and then the slide 26 is placed inside the frame 24. The retainer 34 is then fitted over a part of the slide 26 and into one end of the frame 24 to hold the slide 26 and other parts in place. This subassembly is then slid into the housing 22 and held in place by the snugness of the fit and by a connection between a portion of the plastic housing 22 and a mating portion of the frame 24 (see features 54 and 55 as illustrated in FIGS. 6 and 12, respectively).

A rubber wiper 36 extends laterally across the opening 20 to the defined receiving space 40. As the transducer printed wiring board 13 is slid into the receiving space 40, the rubber wiper 36 wipes the contact pad surface of the printed wiring board 13 free of debris.

It is a common practice for health care providers to apply an acoustic gel between the patient's skin and the transducer to improve the quality of the displayed image. The gel is applied by hand and has a tendency to coat gradually everything that the health care providers touch, including the transducer module printed wiring board 13.

If not wiped off the contact pad surface of the printed wiring board 13, the gel works its way into the contact module 32 and hardens over time. The hardened gel interferes with the proper operation of the contact springs within the contact module 32. The rubber wiper 36 removes the larger pieces of gel and other debris from the contact surface as the transducer printed wiring board 13 is slid into the receiving space 40, thus prolonging the useful life of the contact module 32.

FIG. 3 is an end, cross-sectional view taken through FIG. 2 along the line 3—3, looking in the direction of the arrows. The handle 16 is shown in the unlocked position as in FIG. 2. The offset needle bearing 44 has pushed the cam 46 and the attached slide 26 to the upper limit of its movement within the frame 24. The frame 24 forms an enclosed cage at the top, bottom and two sides of the slide 26. The slide 26 is open at the bottom to accommodate the inserted transducer printed circuit board 13.

As illustrated in FIG. 3, an overhanging ledge 48 extends along two opposed sides of the contact module 32. Two opposed rails 50 at the sides of the slide 26 engage the overhanging ledge 48, lifting the contact module 32 away from the inserted transducer printed wiring board 13 while the handle 16 is in the unlocked position. Opposed reference edges 52 of the transducer printed wiring board 13 are guided by the two opposed rails 50, laterally locating the printed wiring board 13 within the receiving space 40.

FIG. 4 is a side, cross-sectional view of the receptacle assembly shown in a locked position. The parts illustrated are the same as those shown in FIG. 2. The handle 16 is shown rotated approximately 90 degrees in a counterclockwise direction into a locked position, causing the offset needle bearing 44 and the cam 46 to force the slide 26 to the bottom of its travel within the frame 24.

FIG. 5 is an end, cross-sectional view taken through FIG. 4 along the line 5—5, looking in the direction of the arrows. The downward movement of the slide 26 forces the load pad 28, the system printed wiring board 30 and the contact module 32 down against the transducer printed wiring board 13. The opposed contact pads of the two printed wiring boards 30, 13 deform the individual contact springs within the contact module 32. The load pad 28 is made of an elastic material such as rubber and deforms to distribute force evenly over the contact pad surface.

The two opposed rails 50 along the sides of the slide 26 slidably mate with the opposed reference edges 52 of the transducer printed wiring board 13, maintaining a lateral alignment of the transducer printed wiring board 13 with respect to the contact module 32.

In a preferred embodiment of the present invention, the slide moves approximately 0.080" between the unlocked and the locked positions. In doing so, the load pad compresses approximately 0.025". Before compression, the unloaded contact springs within the contact module 32 extend approximately 0.009" above and below the contact module.

RECEPTACLE ASSEMBLY HOUSING, FIGS. 6–11

FIGS. 6–11 illustrate the housing 22 of the receptacle assembly 14 shown in FIG. 2. The housing is hollow inside and provides support for the assembled frame 24, slide 26, load pad 28, system printed wiring board 30, contact module 32 and retainer 34.

FIG. 6 is a top view of the housing 22 which includes the recess 15 into which the handle 16 (not shown) folds in the locked position. An opposed pair of tabs 54 mate with compatible recesses 55 in a portion of the frame 24 (see FIG. 12). FIG. 7 is a side view of the housing 22. FIG. 8 is an end view of the housing 22 taken from the right hand end of FIG. 7. The recess 15 extends from one end of the housing 22 to the other end. FIG. 9 is a bottom view of the housing. FIG. 10 is a side, cross-sectional view of the housing taken along the line 10—10 of FIG. 8, looking in the direction of the arrows. The housing 22 includes an interior space 56 which is open at the right hand end to permit insertion of the assembled components, and includes an opening 58 at the left hand end. During final assembly, the cable strain relief 20 (FIG. 1) is inserted into the opening 58. The opening 58 is visible also in FIG. 8. FIG. 11 is a top, cross-sectional view taken along the line 11—11 of FIG. 7, looking in the direction of the arrows.

FRAME, FIGS. 12–17

FIGS. 12–17 illustrate the frame 24 of a preferred embodiment of the present invention. The handle 16 is pivoted from the pivot pin 42 located in the frame 24. The frame 24 forms an enclosure around the movable slide 26. The load pad 28, the system printed wiring board 30, and the contact module 32 reside within the movable slide 26. Finally, the retainer 34 forms one end of the enclosure formed by the frame 24. In a preferred embodiment, the frame is machined from 7075-T6 aluminum stock.

Figure 13:
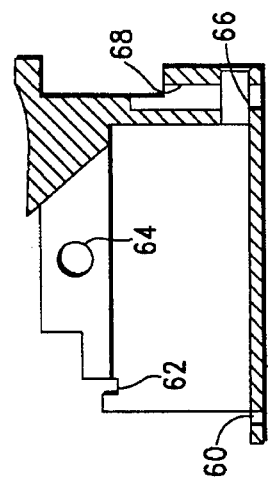
FIGS. 12–17 illustrate a frame, part of the receptacle assembly of FIG. 2.

FIG. 12 is a top view of the frame 24 which includes a slot 60 for accepting part of the retainer 34. The recesses 55 mate with opposed tabs 54 of the plastic housing 22 for retaining the subassembly 23 (see FIG. 2) within the housing 22. FIG. 13 is a side, cross-sectional view of the frame 24, taken along the line 13—13 of FIG. 14, looking in the direction of the arrows. The frame 24 includes the slot 60, a notch 62 for engaging a part of the retainer 34, a bore 64 into which the pivot pin 42 is inserted to provide support and a center of rotation for the handle 16, an entry way 66 to the body of the frame 24 for insertion of the transducer printed wiring board 13, and a recess 68 into which the rubber wiper 36 is inserted.

Figure 16:
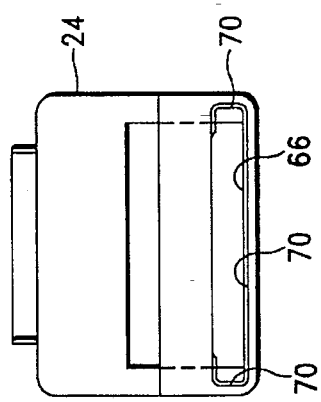
Figures 14, 15:
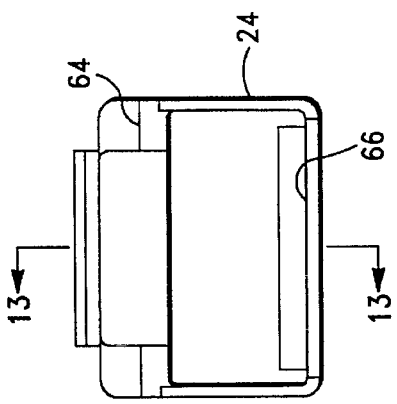
Figure 17:
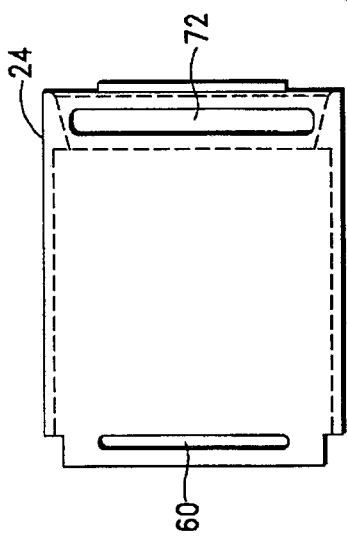

FIG. 14 is an end view of the frame 24 taken from the left end of FIG. 15. FIG. 14 illustrates the pivot pin bore 64 and the entry way 66. FIG. 15 is a side view of the frame 24, illustrating the retainer notch 62 and the pivot pin bore 64. FIG. 16 is an end view of the frame 24 taken from the right end of FIG. 15. The entry way 66 is machined so that a portion of its lower and side edges includes a slight bevel 70 to ease the insertion of the transducer printed wiring board 13. FIG. 17 is a bottom view of the frame 24, illustrating the retainer slot 60 and a machining artifact 72 resulting from the machining of the wiper recess 68.

SLIDE, FIGS. 18–23

FIGS. 18–23 illustrate the slide 26 of the preferred embodiment of the receptacle assembly of FIGS. 2–5. The slide has a top 74, two sides 76, and one end 78, and is open at the other end and at the bottom. The cam 46, which engages the offset needle bearing 44 for raising and lowering the slide within the frame, forms part of the top of the slide 26.

FIG. 18 is a top view of the slide 26 showing the top 74 and the cam 46. FIG. 19 is a side, cross-sectional view of the slide taken along the line 19—19 of FIG. 20 and looking in the direction of the arrows. The open end of the slide includes a pair of tabs 82 which engage a slot located at each side of the system printed circuit board 30. The closed end 78 of the slide includes an opening 84 for accepting the transducer printed wiring board 13.

FIG. 20 is an end view of the slide 26, taken from the left end of FIG. 21. The two tabs 82 extend downward from the top 74 for engaging a corresponding pair of slots along each side of the system printed wiring board 30. This engagement captures the system printed wiring board 30 and maintains a coarse mechanical alignment within the slide 26.

FIG. 21 is a side view of the slide 26, illustrating one side 76 and the cam 46. FIG. 22 is an end view of the slide 26, taken from the right end of FIG. 21. The opening 84 at the bottom of the closed end 78 clears the transducer printed wiring board 13. The opening 84 includes the opposed side rails 50 which slidably mate with the reference edges 52 of the printed wiring board 13 to laterally locate the printed wiring board 13 within the defined receiving space 40 (FIGS. 2–5).

FIG. 23 is a bottom view of the slide 26. Hidden lines illustrate a pair of ledges 85 which lift the contact module 32 away from the transducer printed wiring board 13 when the handle 16 is rotated to the unlocked position.

RETAINER, FIGS. 24, 25

Figure 25:
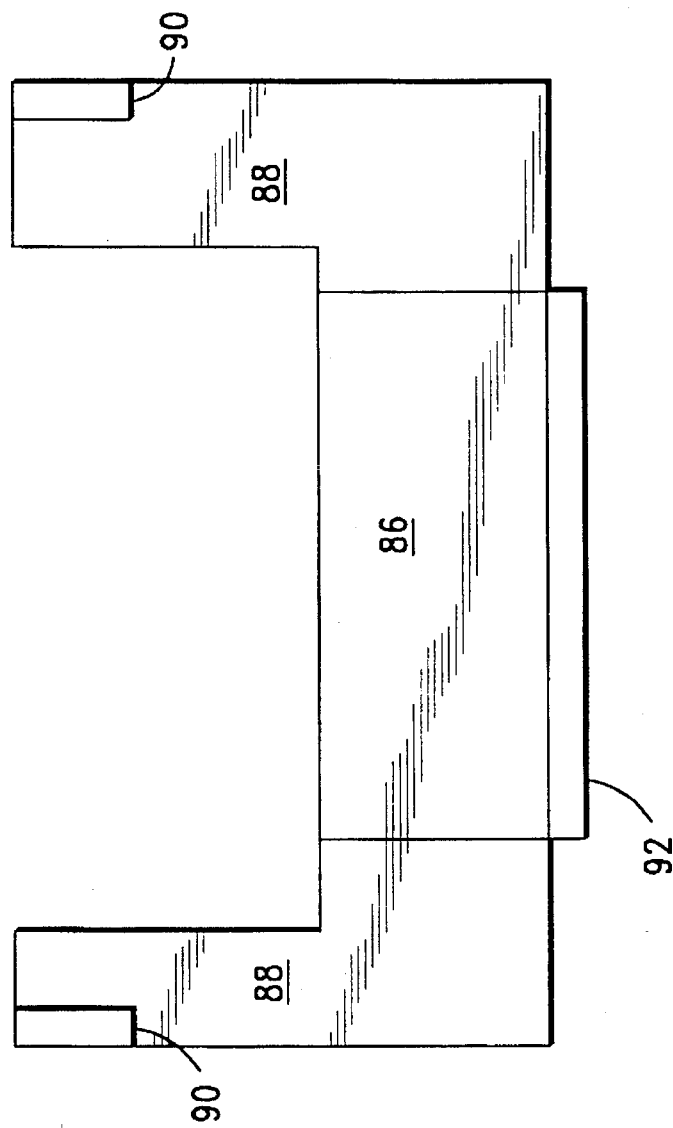
FIGS. 24 and 25 illustrate a retainer, part of the receptacle assembly of FIG. 2.
Figure 24:
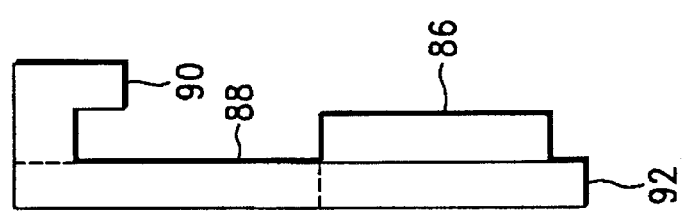

FIGS. 24 and 25 illustrate a retainer 34 for use with the receptacle assembly shown in FIG. 2. FIG. 24 is a side view of the retainer from the left side of FIG. 25. FIG. 25 is a plan view of the retainer. The retainer 34 is U-shaped, having a bottom portion 86 and a pair of opposed legs 88 extending upwardly at the ends. The bottom portion 86 includes a tab 92 which is inserted into the slot 60 of the frame 24 during assembly. The legs 88 extend through cutouts 188 along two sides of the system printed wiring board 30 (see FIG. 32), and prevent the system board 30 from moving out of a preferred alignment when the handle 16 is in the unlocked position.

LOAD PAD, FIG. 26

Figure 26:
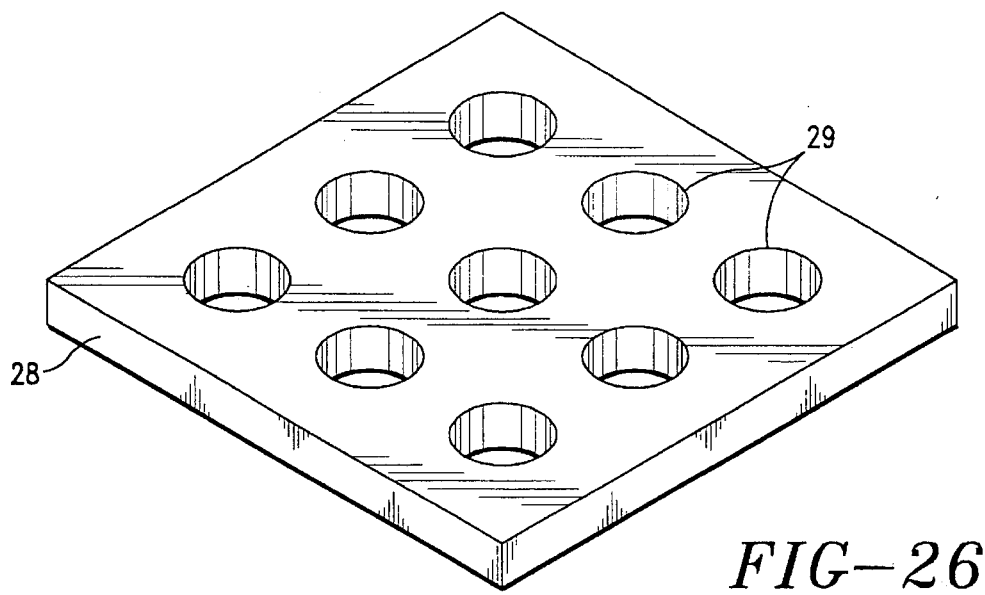
FIG. 26 is a perspective view of a load pad, part of the receptacle assembly of FIG. 2.

FIG. 26 is a perspective view of the compressible load pad 28. The load pad 28 is made of a compressible material such as silicone rubber, which has good memory. In a preferred embodiment, the pad 28 is cut from a sheet of silicone rubber, 0.062" thick. The pad 28 includes the round holes 29 which are placed to adjust the force which is applied by the load pad 28 to the system printed wiring board 30 when the handle 16 is rotated into the locked position. The force is also a function of the stiffness of the rubber, as expressed in the durometer scale.

CONTACT MODULE, FIG. 27

Figure 27:
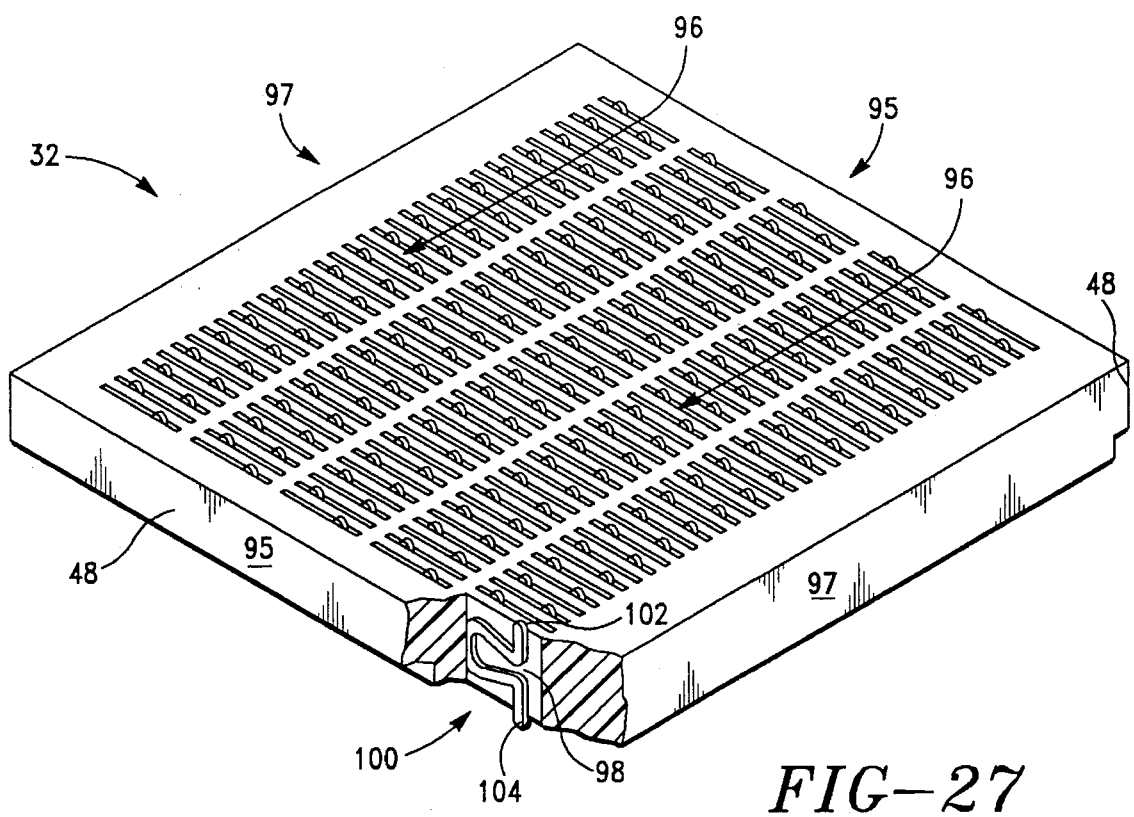
FIG. 27 is a cut away, perspective view of a contact module for use with the receptacle assembly of FIG. 2.

FIG. 27 is a cut away, perspective view of one embodiment of a contact module 32 for use with the receptacle assembly of FIG. 2 (additional embodiments of a contact module suitable for use with the modular transducer 10 are illustrated in FIGS. 32–37, described below). The contact module 32 includes a nest block 94 having rows of slots 96 and opposed sides 95 and 97. A portion of the nest block 94 is cut away to reveal a typical slot 98 including a contact spring 100 having an upper contact 102 and a lower contact 104. In the uncompressed state, the contacts 102, 104 extend approximately 0.009" beyond the nest block 94.

The upper portion of two opposed sides 95 of the nest block extend beyond the lower portion of the sides, creating opposed overhangs 48. The overhangs 48 engage the ledges 85 (FIG. 23) of the rails 50 along the sides of the slide 26, permitting the slide to lift the contact module 32, enlarging the receiving space 40 when the handle 16 is rotated into the unlocked position. The opposed sides 95—95 and 97—97 of the contact module 32 are used to align the contact module 32 within the slide 26 and the receiving space 40.

MODULAR TRANSDUCER MODULE, FIGS. 28 AND 29

Figure 28:
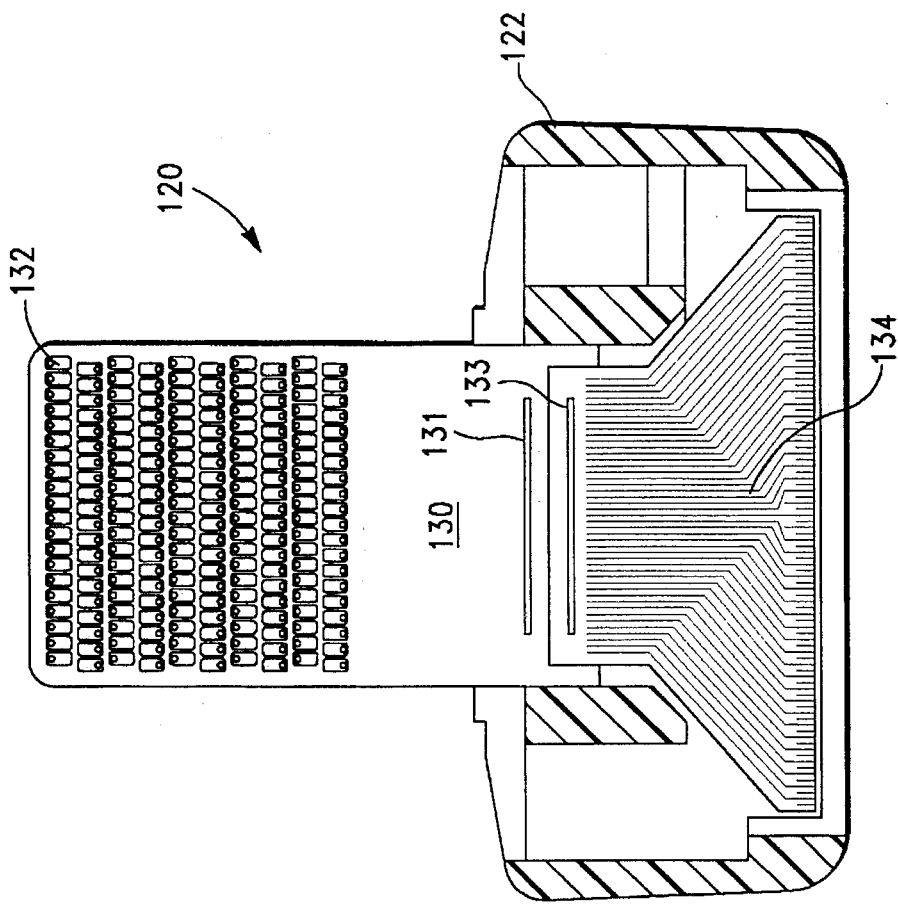
FIGS. 28 and 29 illustrate a preferred embodiment of an ultrasound transducer module according to another aspect of the present invention, and for use with the receptacle assembly of FIG. 2.
Figure 29:
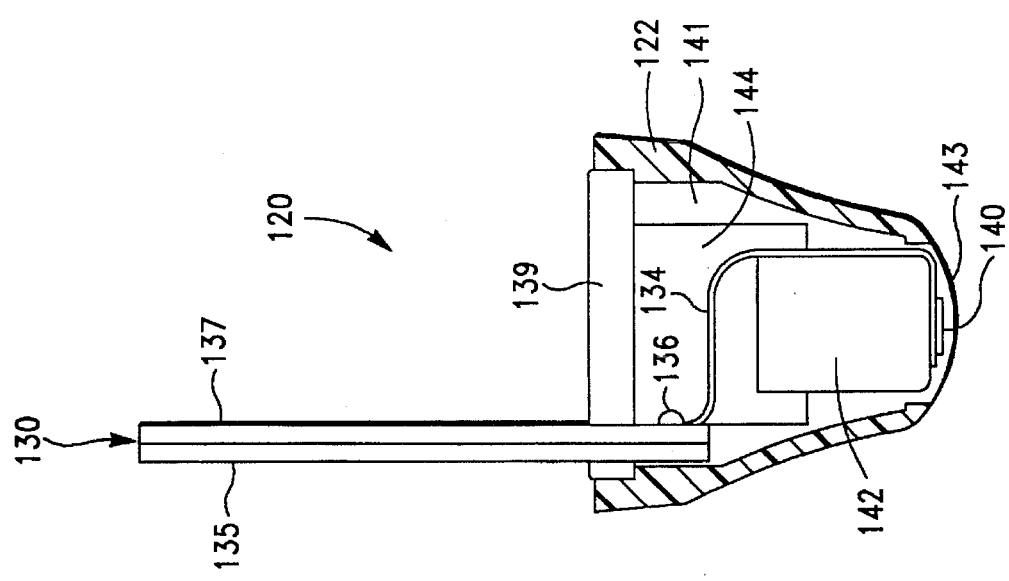

FIGS. 28 and 29 illustrate a preferred embodiment of an ultrasound transducer module according to another aspect of the present invention, and for use with the receptacle assembly of FIG. 2.

FIG. 28 is a profile, cross-sectional view of one embodiment of the ultrasound transducer module, indicated generally by the numeral 120. The ultrasound transducer module 120 includes a multitude of piezo-electric elements arranged in a linear array 140, a flex circuit 134, an interface board 130, an electrical and mechanical interconnect 136 between the flex circuit 134 and the interface board 130, a backing block 142, a housing 122, an acoustic lens 143, a top cap 139 and internal potting 141.

In an imaging system employing phased array ultrasound, the scan head includes a multitude of independent piezo-electric elements arranged in a linear array such as the ultrasound transducer 140. Such an array is disclosed in U.S. Pat. Nos. 4,550,607 and 4,669,009, each of which has been incorporated by reference. Typically, each element of the linear array is independently controlled by a separate coaxial signal line within the transducer assembly interfacing cable (e.g., cable assembly 18 of FIG. 1).

In the embodiment illustrated in FIGS. 28 and 29, each piezo-electric element of the array 140 is capable of converting an electrical signal from the electrical conductor in the flex circuit 134 to sound. This sound is transmitted through the acoustic window 143 (also referred to as an acoustic lens) into some portion of a patient's body. Sound reflected by internal structures of the patient's body is returned back through the acoustic window 143 to the array of piezo-electric elements 140. Each piezo-electric element of the array 140 converts the reflected sound energy to an electrical signal which is conveyed to the corresponding electrical conductor in the flex circuit 134.

Besides the piezo-electric array 140, the acoustic section of the transducer module 120 includes a backing block 142 which is the mechanical foundation for the array. In addition, the backing block 142 is fabricated from materials which are acoustically lossy. Sound energy emitted from the back sides of the acoustic array 140 is absorbed so that it does not return to the piezo-electric array 140, since sound from the back side would produce ambiguous and undesired electrical signals in the array of piezo-electric elements 140.

The interface board 130 includes a signal carrying printed wiring board 137 and an interface board backing 135 which have been laminated together using glass-epoxy pre-preg during their manufacture. The printed wiring board 137 is used to transfer the bi-directional electrical signals from the receptacle assembly (FIG. 1) to the conductors in the flex circuit 134. The signal carrying in the printed wiring board 137 includes contact pads 132 with interface to the spring contacts 102 in the receptacle assembly. The printed wiring board 137 includes a row of interconnect pads 131 which correspond to similar pads 133 on the flex circuit 134. Bi-directional electrical signals are conveyed from the contact pads 132 to the interconnect pads 131 by printed circuitry on inner layers of the printed wiring board 137. The electrical interconnection between pads 131 and pads 133 is accomplished with wire bonding or with a solder bridge 136.

The contact pads 132 are plated with hard gold both on their surfaces and their edges. The co-pending U.S. patent application entitled "Submersible Connector System", Attorney's Docket No. ACUS-01-003/TD-32, filed Oct. 4, 1995, teaches a preferred method for plating the contact pads 132. In a preferred embodiment, the printed wiring board 137 has 12 layers evenly spaced. The interface board backer 135 can be made from either glass-epoxy laminate, or from a thermal plastic such as Radel. The purpose of the board backer 135 is to isolate electrically and to protect the circuitry on the back side of the printed wiring board 137.

In one embodiment, the total thickness of the interface board 130 is 0.093". All holes in the printed wiring board 137 are drilled and plated through. The copper areas of the outer layers are plated with about 50 micro-inches of hard gold over nickel. The co-pending patent application entitled "Submersible Connector System" and incorporated by reference describes a preferred method used to plate both the surfaces and the edges of the circuitry on the front surface 132 of the interface board 130.

The mechanical parts required to complete the transducer module 120 include the housing 122, the cap 139 and internal potting material 141. An example of a suitable material 141 is a silicone rubber elastomer supplied by Loctite Corp., No. 1022 RTV. The internal potting material 141 provides strain relief and prevents corrosive fluids from intruding into the interior of the assembly 120 and damaging the array of piezo-electric elements 140, the flex wiring 134, and the interconnect 136. The cap 139, the housing 122, and the printed wiring board 130 provide a rigid and dimensionally stable relationship between contact pads 132, the housing 122, and the receptacle assembly (FIG. 1) with which this transducer module interfaces.

SYSTEM PRINTED WIRING BOARD, FIG. 30

FIG. 30 is a perspective view from the bottom (contact pad) side of the system printed wiring board 30 used with the receptacle assembly 14 of FIG. 2. The system board 30 includes an area 180 having contact pads 182 (a representative number of these pads is illustrated) and another area 184 having wiring terminations. The board 30 also includes a pair of recesses 188 located at two opposed sides. The recesses 188 engage the legs 88 of the retainer 34.

RUBBER WIPER, FIG. 31

FIG. 31 is a perspective view of the rubber wiper 36, which is part of the receptacle assembly of FIG. 2. The wiper 36 has a wiping blade portion 190 which wipes the contact pad surface of the transducer module printed wiring board 13 when the module is inserted into the receiving space 40 of the receptacle assembly 14. In a preferred embodiment, the wiper 36 is molded from neoprene rubber.

ALTERNATIVE EMBODIMENTS OF A CONTACT MODULE, FIGS. 32–37

FIGS. 32–37 illustrate a variety of embodiments of the contact module 32 used to make electrical connection between the opposed contact pads.

Figure 32:
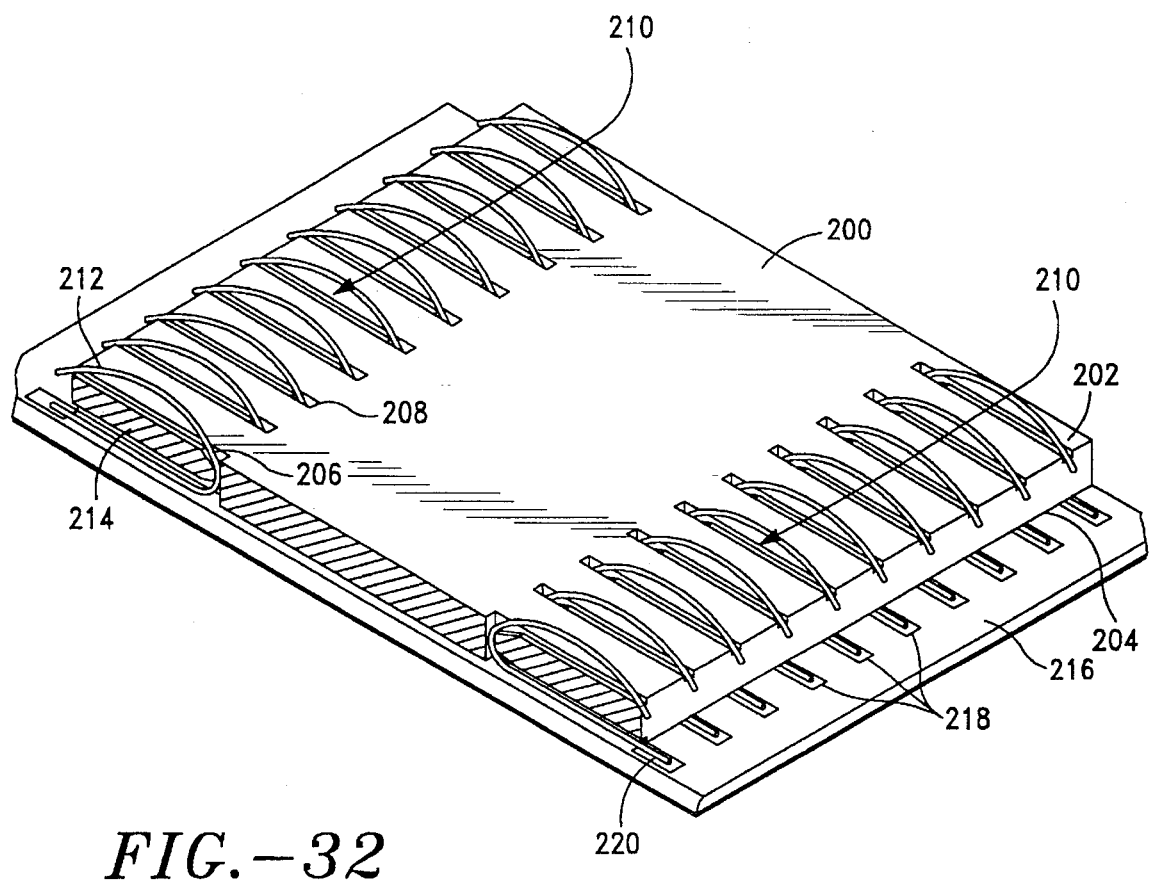
FIG. 32 is a partial perspective view of an embodiment of a contact module using surface mount technology.

FIG. 32 is a partial perspective view of an embodiment of a contact module using surface mount technology. The figure illustrates a planar body 200, having a contact surface 202, a mounting surface 204, a plurality of U-shaped contact springs 206 located within nests 208, arranged in parallel rows 210. Each contact spring 206 includes a curved contact arm portion 212 and a flat mounting arm portion 214. The assembly of body 200 and contact springs 206 is surface mounted on a printed wiring board 216. The board 216 includes surface mount pads 218 for making a solder connection between an extended portion 220 of the mounting arm portion 214 and a surface mount pad 218. The body 200 is preferably made of an LCP plastic.

The system printed wiring board 30 of FIG. 2 is modified to permit attachment of the surface mount contact module as illustrated in FIG. 32. In FIG. 32 a portion of the modified system printed wiring board is shown as element 216. Printed wiring (not shown) within the modified system printed wiring board 216 connects individual signal lines to the surface mount pads 218 and hence to the individual contact springs 206, In a preferred embodiment, the springs 206 are located on 0.040" centers and are aligned within the receptacle assembly 14 (FIG. 2) with corresponding contact pads of the transducer module printed wiring board 13.

When the operating handle 16 is rotated from the unlocked (FIG. 2) to the locked (FIG. 4) position, the curved contact arm portion 212 is forced against an opposed contact pad of the transducer module printed wiring board 13. Displacement of the contact point between the curved arm portion 212 and the opposed contact pad results in a wiping action of the curved arm portion 212 across the contact pad, establishing a more reliable electrical connection between the individual conductors of the system cable 18 and the piezo-electric elements 140 of the modular transducer.

Figure 33:
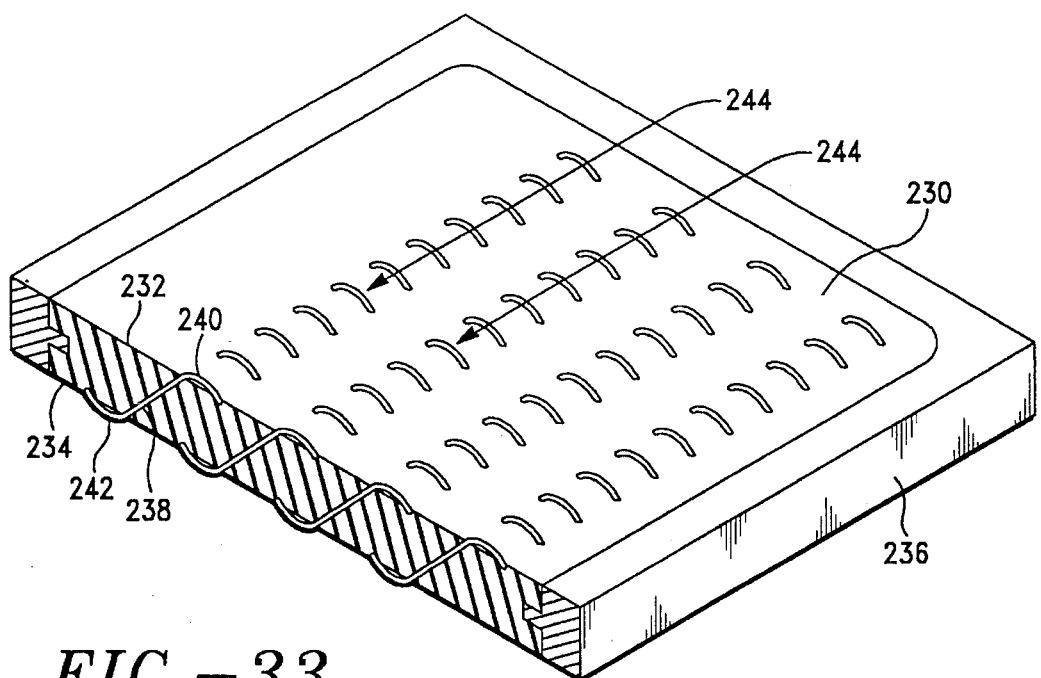
FIG. 33 is a partial perspective view of an elastomeric contact module having embedded conductive elements.

FIG. 33 is a partial, perspective view of an elastomeric contact module used to provide a reliable electrical connection between the contact pads on the system printed wiring board 30 and the contact pads on the transducer module printed wiring board 13. The contact module in this embodiment includes a planar base 230 made of an elastomer silicone rubber, supported on four sides by a frame 236. Formed wire contacts of steel or beryllium-copper are disposed within the elastomer silicone rubber in parallel rows 244. Portions 240 and 242 of each formed wire contact 238 extend beyond opposed surfaces 232 and 234, respectively, of the planar base 230. In a preferred embodiment, the formed wire contacts 238 are plated with nickel and a 50 micron thickness of hard gold. The opposed contact pad pairs of the two printed wiring boards 30, 13 (FIG. 2) are offset to correspond with an offset between the portions 240 and 242 of each formed wire contact 238.

When the elastomeric contact nest is sandwiched between opposed printed wiring boards, a compressive force from contact with a pad on a printed wiring board will result in a lateral displacement of the portions 240, 242 of the formed wire contacts 238. This displacement will produce the wiping action essential for establishing a reliable electrical connection.

Figure 34:
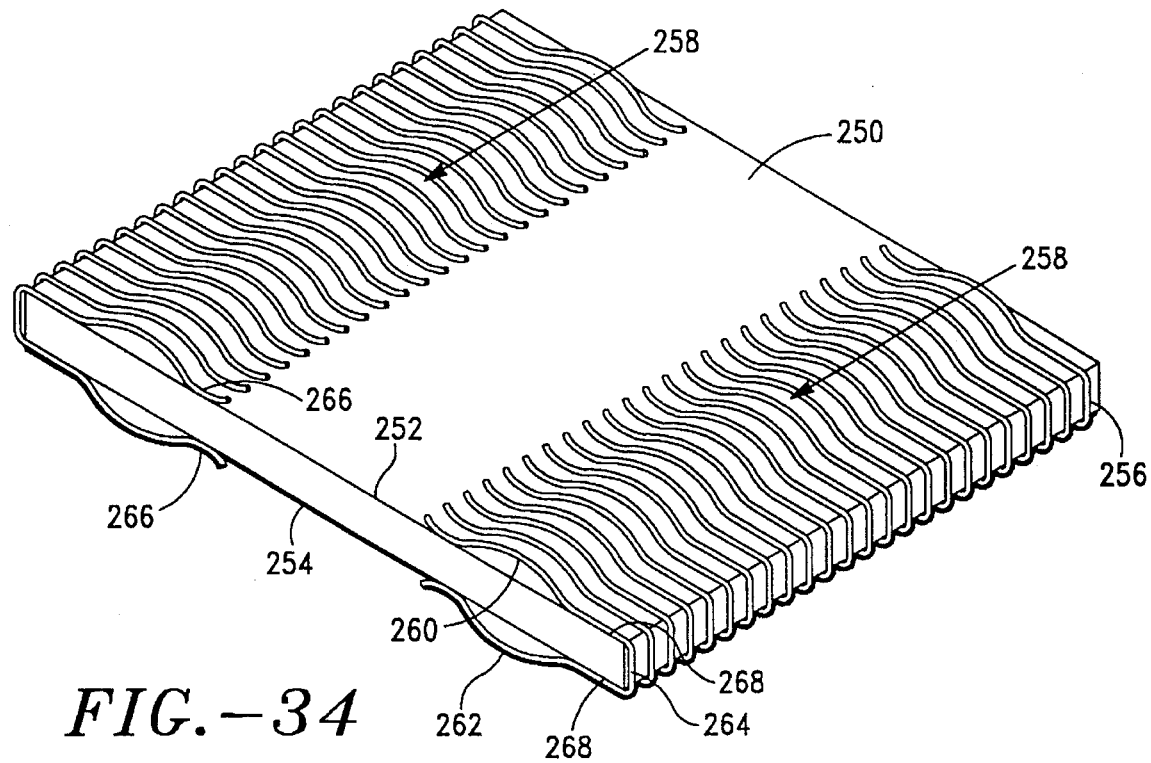
FIG. 34 is a partial perspective view of another embodiment of a contact module suitable for use in the modular transducer system of FIG. 1.

Another embodiment of a contact module is illustrated in FIG. 34, a perspective view. The module includes a printed wiring board 250 having opposed planar surfaces 252 and 254, a plurality of U-shaped formed wire spring contacts 256 arranged in parallel rows 258. Each U-shaped spring contact 256 includes opposed curved portions 260 and 262 joined by an end section 264. Each of the curved portions 260, 262 terminates in a outwardly curved tip 266. The printed wiring board 250 includes isolated solder pads 268 disposed on the opposed surfaces 252, 254 for solder attachment of the spring contacts 256 to the printed wiring board 250.

For operation, this contact module is compressed between the system printed wiring board 30 (FIG. 2) and the transducer module printed wiring board 13. As the rotation of the operating handle 16 narrows the separation between the opposed printed wiring boards 30, 13, the curved portions 260, 262 of the contact springs 256 establish a point of contact with opposed contact pads. The compressive force causes a lateral displacement of this point of contact across the contact pads resulting in the wiping action needed to secure a reliable electrical connection.

Figure 35:
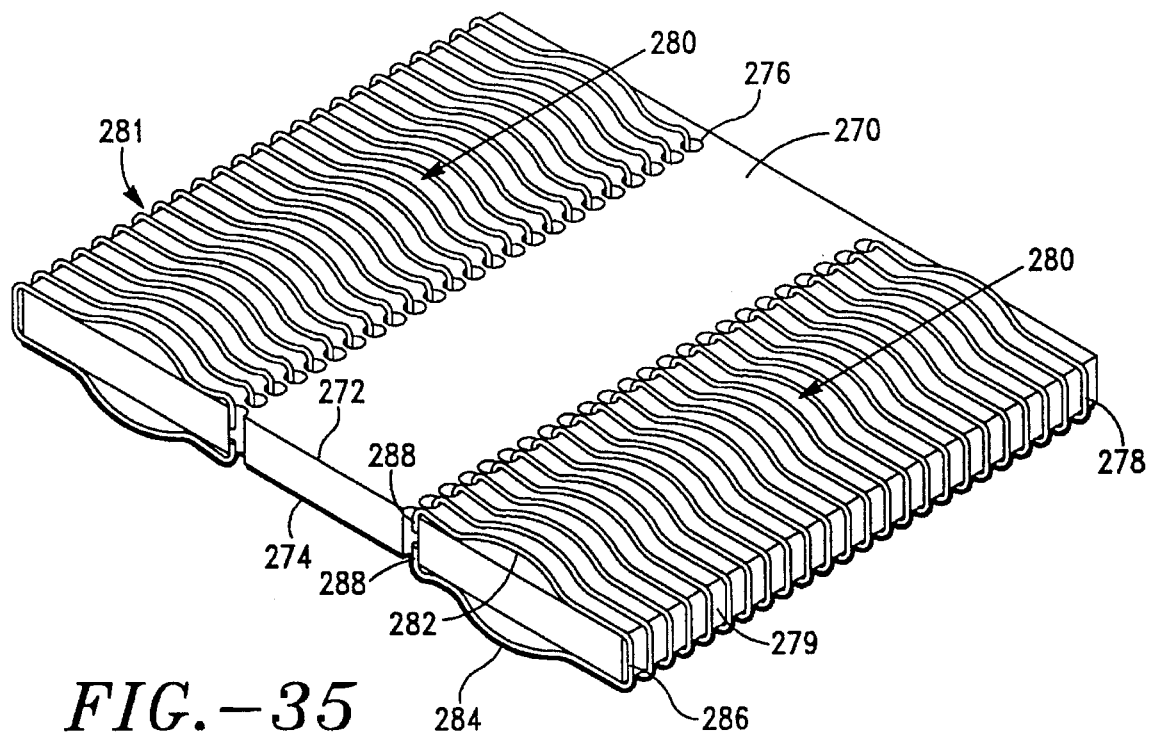
FIG. 35 is a partial perspective view of a variation of the contact module shown in FIG. 34.

FIG. 35 is a perspective view illustrating a variation of the contact module shown in FIG. 34. The module includes a printed wiring board 270 having opposed planar surfaces 272, 274, and holes 276. Individual U-shaped formed wire contact springs 278 are arranged in parallel rows 280, along opposed edges 279, 281. Each U-shaped contact spring 278 includes curved portions 282, 284 for making electrical contact with opposed contact pads, and a mid-section 286. One end 288 of each curved portion is folded into one hole 276. Each spring is attached by solder to solder pads disposed near the opposed edges 279, 281.

The module shown in FIG. 35 is compressed between opposed printed wiring boards resulting in displacement of a contact point to produce the needed wiping action as discussed above.

big. 36 is a perspective view of an embodiment of a contact module using flex circuit to connect the opposed contact pads. The flex circuit contact module includes a printed wiring board 290 having opposed planar surfaces 292, 294 and a pair of cylindrical members 296 disposed along two opposed edges. Each cylindrical member 296 includes a notch along one side for engaging a key-like extension 298 of the printed wiring board 290 for attachment to the printed wiring board. The cylindrical members 296 are preferably made of an elastomer, and the notch is preferably bonded to the key-like extension 298.

A piece of flex circuit 300 is wrapped around each cylindrical member 296 and the ends are attached to the opposed surfaces 292, 294 of the printed wiring board 290. Each piece of flex circuit 300 includes a plurality of parallel, electrically insulated conductors 301. The flex circuit 300 defines an outer surface 302 extending from one surface 292 to the opposed surface 294 of the printed wiring board 290. The insulation is stripped from a portion of the outer surface 302 to permit electrical contact with the conductors 301.

The flex circuit contact module is placed between opposed printed wiring boards 30 and (FIG. 2) such that the portion of the exposed conductors 301 which wrap around the cylindrical members 296 comes into contact with the opposed contact pads. The elastomer cylindrical members 296 insure compliance. A slight wiping action occurs because of the way the elastomer distorts under pressure. In a preferred embodiment, the exposed flex circuit conductors 301 are gold plated.

Finally, FIG. 37 illustrates an embodiment of a contact module using a Z-axis material, such as part nomenclature CP-ECPI, available from AT&T Microelectronics, 555 Union Blvd., Allentown, Pa. 18103. The Z-axis material is an elastomeric conductive polymer interconnect which conducts across its thickness only and has nearly infinite resistance in the lateral direction. An enlarged portion 312 of the conductive polymer interconnect illustrates the many conductive elements which make up the material. When sandwiched between opposed contact pads 314, 316, the Z-axis material 310 establishes a reliable low-impedance electrical connection between the opposed pads and insulates adjacent pads from one another.

While the foregoing detailed description has described several embodiments of a modular transducer system in accordance with this invention, it is to be understood that the above description is illustrative only and is not limiting of the disclosed invention. It will be appreciated that another mechanism which provides mechanical support and electrical connection between opposed contact pads disposed on two printed wiring boards, one board connected to an ultrasound transducer, the other to microcoaxial cables, and a contact module interposed between the opposed contact pads is within the scope and spirit of this invention. Thus the invention is to be limited only by the claims as set forth below, and legal equivalents thereof.

What is claimed is:

1. A modular transducer system, comprising:

an ultrasound transducer module including an ultrasound transducer and a transducer printed wiring board, the transducer board having a plurality of electrical contact pads disposed on a portion of one surface and connected for carrying electrical signals between the pads and the transducer;

a system printed wiring board, the system board having a plurality of electrical contact pads disposed on a portion of one surface in corresponding opposition to contact pads of the transducer board and defining opposed pairs of contact pads, the system board having wiring termination pads spaced apart from the contact pads, and predetermined contact pads being electrically connected with predetermined wiring termination pads;

a contact module located between the transducer board and the system board, the contact module having a system surface and an opposed transducer surface, and electrical conductors extending between the opposed surfaces and aligned with opposed pairs of contact pads; and aligning and clamping means for supporting the system board, the contact module, and the transducer board, for aligning the opposed pairs of contact pads with corresponding contact module conductors, and for clamping the contact pad portion of the transducer board and the system board to the contact module, whereby an electrical connection is established between the system board and the ultrasound transducer, and the transducer module is supported by the aligning and clamping means.

2. The modular transducer system as set forth in claim 1, wherein the ultrasound transducer module is mechanically and electrically interchangeable with any one of a plurality of secondary ultrasound transducer modules, and wherein the aligning and clamping means defines a receiving space for the contact pad portion of the transducer board, and the aligning and clamping means includes means for unclamping and releasing the transducer board from the receiving space, permitting any secondary transducer module to be interchanged with the ultrasound transducer module.

3. The modular transducer system as set forth in claim 2, wherein a subset of the transducer board contact pads are connected to provide a transducer module identification code.

4. The modular transducer system as set forth in claim 3, defining classes of transducer acoustic and electrical characteristics, each ultrasound transducer module being a member of one defined class, and the class being identified by a predetermined module identification code.

5. The modular transducer system as set forth in claim 2, wherein the aligning and clamping means and the means for unclamping and releasing include an operating handle and define an unlocked position and a locked position of the receiving space, and in the unlocked position the transducer board is unclamped within the receiving space and in the locked position the transducer board is clamped within the receiving space.

6. The modular transducer system as set forth in claim 5, further including a housing enclosing the aligning and clamping means, the means for unclamping and releasing, and the system board and the contact module, the operating handle extending outside the housing, and the housing having an opening to the defined receiving space for inserting and withdrawing the contact pad portion of a transducer module printed wiring board.

7. The modular transducer system as set forth in claim 6, wherein the housing, the aligning and clamping means, the means for unclamping and releasing, the system board, the contact module and the operating handle define a receptacle assembly.

8. The modular transducer system as set forth in claim 2, further including the transducer module having a housing enclosing the ultrasound transducer, the housing being attached to and forming a fluid seal with the transducer board, whereby the transducer module is submersible in a sterilizing fluid.

9. The modular transducer system as set forth in claim 8, further including the interchangeable transducer module being keyed to the aligning and clamping means permitting insertion of the contact pad portion of the transducer board into the defined receiving space such that the transducer board contact pads are adjacent the contact springs.

10. The modular transducer system as set forth in claim 1, further including a system cable assembly having a plurality of microcoaxial cables connected to the system wiring termination pads.

11. A receptacle assembly for use in an ultrasound modular transducer system, comprising:

a system printed wiring board having a plurality of electrical contact pads disposed on one surface and having wiring termination pads connected to the contact pads;

a contact module having a plurality of compressible, electrically conductive elements aligned in opposition with the system board contact pads; and aligning and clamping means defining a receiving space for an ultrasound transducer module printed wiring board having electrical contact pads disposed in opposition to the aligned electrically conductive elements, for supporting the system board and the contact module, for providing support for a printed wiring board within the defined receiving space, and for clamping the two boards and the contact module, whereby an electrical connection is established between opposed contact pads and the received board is supported.

12. The receptacle assembly as set forth in claim 11, wherein the system board includes microcoaxial cable terminations connected to the wiring termination pads.

13. The receptacle assembly as set forth in claim 11, wherein the aligning and clamping means includes means for unclamping and releasing a received transducer module printed wiring board, and includes an operating handle defining an unlocked position and a locked position of the receiving space, wherein the received board is unclamped in the unlocked position, and is clamped in the locked position.

14. The receptacle assembly as set forth in claim 13, wherein the aligning and clamping means includes means for lifting the contact module clear of the receiving space when the operating handle is rotated from the locked position to the unlocked position, whereby the contact module does not interfere with the insertion or removal of a transducer module printed wiring board.

15. The receptacle assembly as set forth in claim 11, defining a contact pad region of the system printed wiring board, and wherein the aligning and clamping means includes a compliant member for distributing force uniformly across the defined contact pad region to insure a reliable electrical contact with the contact pads of a received transducer printed wiring board.

16. The receptacle assembly as set forth in claim 15, wherein the compliant member is a compressible rubber pad.

17. The receptacle assembly as set forth in claim 11, wherein the contact module includes a body for supporting the electrically conductive elements and for cooperating with the aligning and clamping means to align the electrically conductive elements with respect to corresponding opposed contact pads.

18. The receptacle assembly as set forth in claim 17, wherein the electrically conductive elements and the system printed wiring board electrical contact pads are gold plated.

19. The receptacle assembly as set forth in claim 17, wherein the electrically conductive elements are compressible spring members, and wherein the body forms a nest of the compressible spring members.

20. A receptacle assembly for use in an ultrasound modular transducer system, comprising:

a system printed wiring board having a plurality of electrical pads disposed on one surface and having wiring termination pads connected to the electrical pads;

a contact module having a plurality of compressible, electrically conductive elements aligned in opposition with the electrical pads of the system printed wiring board;

aligning and clamping means defining a receiving space for an ultrasound transducer module printed wiring board having electrical contact pads disposed in opposition to the aligned, electrically conductive elements, for supporting the system board for providing support for a printed wiring board within the defined receiving space, and for clamping the two boards and the contact module; and the aligning and clamping means including means for unclamping and releasing the transducer module printed wiring board from the defined receiving space, and including an operating handle defining an unlocked position and a locked position such that in the unlocked position the transducer module printed wiring board is unclamped within the receiving space and in the locked position the transducer module printed wiring board is clamped within the receiving space.

21. The receptacle assembly as set forth in claim 20, wherein the system printed wiring electrical pads define contact pads, the contact module supports the electrically conductive elements and cooperates with the aligning and clamping means to align the electrically conductive elements with respect to corresponding opposed contact pads.

22. The receptacle assembly as set forth in claim 21, wherein the electrically conductive elements are compressible spring members, and wherein the body forms a nest of the compressible spring members.

23. The receptacle assembly as set forth in claim 21, wherein the system printed wiring board electrical pads define contact pads, the contact module includes a portion made of a Z-axis material which provides the electrically conductive elements.

24. The receptacle assembly as set forth in claim 20, wherein the system printed wiring board electrical pads define surface mount pads, the contact module defines a surface mount contact nest supporting the electrically conductive elements, the electrically conductive elements are U-shaped compressible wire spring members having one side attached to corresponding surface mount pads and another side for making contact with the aligned, opposed contact pads of a received transducer module printed wiring board.

25. The receptacle assembly as set forth in claim 20, wherein the system printed wiring board electrical pads define contact pads, the contact module includes a frame supporting an elastomeric contact nest including the electrically conductive elements and cooperates with the aligning and clamping means to align the electrically conductive elements with respect to corresponding contact pads, the elastomeric contact nest defining opposed first and second surfaces, and the electrically conductive elements being formed wire contacts having a center portion supported at an angle with respect to the opposed surfaces and two end portions, one end portion extending outwardly from each opposed surface, the outwardly extending end portions being curved back toward the surface from which each extends to form a sliding contact surface.

26. The receptacle assembly as set forth in claim 20, wherein the system printed wiring board electrical pads define contact pads, the contact module includes a body supporting the plurality of electrically conductive elements and defining two opposed edges, the opposed edges including isolated attachment pads, the electrically conductive elements defining individual U-shaped spring contacts formed of wire and attached to the isolated attachment pads for supporting the spring contacts, the contact module defining opposed first and second surfaces, and cooperating with the aligning and clamping means to align the electrically conductive elements with respect to corresponding opposed contact pads, the spring contacts having a center U-shaped portion for attachment to the respective attachment pads and opposed end sections extending from the U-shaped center portion and forming opposed sliding contact surfaces.

27. The receptacle assembly as set forth in claim 20, wherein the system printed wiring board electrical pads define contact pads, the contact module includes a printed wiring board having opposed planar surfaces and a pair of cylindrical members disposed along two opposed edges, the cylindrical members are made of a compliant material, flex circuit having isolated conductive elements and two opposed ends is wrapped around each cylindrical member and the opposed ends attached to the opposed planar surfaces to form the plurality of electrically conductive elements aligned in opposition with the contact pads, and the contact module cooperating with the aligning and clamping means to align the electrically conductive elements with respect to corresponding opposed contact pads.

28. An ultrasound transducer module, comprising:

an ultrasound transducer formed of a linear array having a plurality of piezo-electric elements;

a backing block for supporting the linear array;

a printed wiring board providing support for the backing block and including a plurality of electrical contact pads connected by printed wiring to interconnect pads; and a flex circuit for connecting the interconnect pads to the piezo-electric elements, whereby an electrical connection is established between the printed wiring board contact pads and the piezo-electric elements.

29. The ultrasound transducer module as set forth in claim 28, further including a protective housing enclosing the ultrasound transducer, the backing block, the flex circuit and at least a portion of the printed wiring board including the interconnect pads.

30. The ultrasound transducer module as set forth in claim 29, wherein the protective housing includes an acoustic window adjacent the piezo-electric elements and opposite the backing block, and the acoustic window is covered by a Cap which is transparent to ultrasound, the cap forming a fluid and dust seal with the protective housing.

31. The ultrasound transducer module as set forth in claim 28, wherein the printed wiring board defines a contact pad region on one surface of the board and the contact pads are disposed within the defined region.

32. The ultrasound transducer module as set forth in claim 31, further including an interface board backing attached to a non-contact pad surface of the printed wiring board for protecting exposed printed wiring and for stiffening the printed wiring board.

33. A modular transducer assembly comprising:

a transducer module having a piezo-electric transducer, a backing block for supporting the piezo-electric transducer, a printed wiring board having contact pads disposed on at least one surface, and means for electrically connecting the piezo-electric transducer to the contact pads;

a cable assembly having means for electrically connecting one end of a cable to the contact pads; and means for mechanically and electrically engaging and releasing the transducer module from the cable assembly, whereby different transducer modules can be engaged by and released from the cable assembly.

34. The modular transducer assembly as set forth in claim 33, wherein the contact pads are disposed on one surface of the transducer module printed wiring board and the cable assembly further includes a printed wiring board having contact pads disposed on one surface in opposition to the transducer module contact pads, and the one end of the cable being electrically connected to the cable assembly printed wiring board contact pads.

35. The modular transducer assembly as set forth in claim 34, wherein the means for mechanically and electrically engaging and releasing the transducer module from the cable assembly includes a frame defining a receiving space for the transducer module printed wiring board, and further includes an operating handle defining a locked position and an unlocked position, the locked position engaging the transducer module printed wiring board within the receiving space and the unlocked position releasing the transducer module.

36. The modular transducer assembly as set forth in claim 35, further including means for aligning the contact pads of the two printed wiring boards in opposition with each other.

37. The modular transducer assembly as set forth in claim 36, further including a contact module located between the printed wiring boards for making a reliable electrical contact between opposed contact pads.

38. The modular transducer assembly as set forth in claim 37, further including means for lifting the contact module clear of the transducer module contact pads within the receiving space when the operating handle is placed in the unlocked position, thereby facilitating the removal and insertion of the transducer module printed wiring board for exchanging one transducer module for another.

39. The modular transducer assembly as set forth in claim 38, wherein the cable assembly printed wiring board is flexible and a compressible member is placed against the non-contact pad surface of the flexible printed wiring board for distributing force equally to each contact pad when the operating handle is placed in the locked position for improving the reliability of the electrical connection between the opposed contact pads.

40. The modular transducer assembly as set forth in claim 39, further including a housing for the transducer module and a second housing for the printed wiring board end of the cable assembly, the operating handle extending outside the second housing, and the second housing having an opening to the receiving space for insertion of the transducer module printed wiring board.

* * * * *